(12) United States Patent
Coombs et al.

(10) Patent No.: US 9,638,553 B2
(45) Date of Patent: May 2, 2017

(54) MODULAR INSPECTION SYSTEM HANDSET

(71) Applicant: General Electric Company, Schenectady, NY (US)

(72) Inventors: Kevin Andrew Coombs, Syracuse, NY (US); Clark Alexander Bendall, Syracuse, NY (US); Joshua Lynn Scott, Jordan, NY (US); Bobby Dale Hournbuckle, Jr., West Henrietta, NY (US)

(73) Assignee: General Electric Company, Schenectady, NY (US)

( * ) Notice: Subject to any disclaimer, the term of this patent is extended or adjusted under 35 U.S.C. 154(b) by 245 days.

(21) Appl. No.: 14/010,068

(22) Filed: Aug. 26, 2013

(65) Prior Publication Data
US 2015/0053025 A1    Feb. 26, 2015

(51) Int. Cl.
| | | |
|---|---|---|
| *G01D 11/30* | (2006.01) | |
| *G01N 29/22* | (2006.01) | |
| *G01N 27/00* | (2006.01) | |
| *G01D 11/24* | (2006.01) | |
| *G01N 21/84* | (2006.01) | |
| *G01N 21/88* | (2006.01) | |

(52) U.S. Cl.
CPC .............. *G01D 11/30* (2013.01); *G01D 11/24* (2013.01); *G01N 21/84* (2013.01); *G01N 27/00* (2013.01); *G01N 29/226* (2013.01); *G01N 21/88* (2013.01); *G01N 2201/024* (2013.01); *G01N 2201/0221* (2013.01)

(58) Field of Classification Search
CPC .......... G01N 21/8806; G01N 21/8803; G01N 29/226; G01N 27/00; G01N 21/84; G01N 2201/024; G01N 21/88; G01N 2201/0221; G01N 27/72; G01N 27/904; G01D 11/30; G01D 11/24; G02B 23/2476
USPC ................... 600/101–187; 73/866.5, 865.8
See application file for complete search history.

(56) References Cited

U.S. PATENT DOCUMENTS

| | | |
|---|---|---|
| 6,007,939 A | 12/1999 | Clowers |
| 6,099,097 A | 8/2000 | Hocker et al. |
| 6,272,717 B1 | 8/2001 | Saraydar |
| 6,656,626 B1 | 12/2003 | Mooty et al. |
| 6,670,808 B2 | 12/2003 | Nath et al. |

(Continued)

OTHER PUBLICATIONS

GE Measurement & Control Solutions; XLG3 Video Probe, Inspection Technologies, 2011, 16 pages.

(Continued)

*Primary Examiner* — Daniel S Larkin
*Assistant Examiner* — Anthony W Megna Fuentes
(74) *Attorney, Agent, or Firm* — Barclay Damon, LLP

(57) ABSTRACT

A handset for inspecting a target object with a sensor in an inspection module is disclosed. The handset includes a housing having a grip portion adapted to be held by a person, the housing adapted to selectively mechanically engage with the inspection module, a handset interface on the housing adapted to exchange signals with the inspection module, a handset processor, a user input interface accessible to the person gripping the grip portion and adapted to provide a control signal to the handset processor, and a user output interface responsive to the handset processor to display the data transmitted by the handset processor about the target object.

16 Claims, 8 Drawing Sheets

(56) References Cited

U.S. PATENT DOCUMENTS

| | | |
|---|---|---|
| 6,697,764 B2 | 2/2004 | Corby, Jr. et al. |
| 6,890,196 B2 | 5/2005 | Vila |
| 7,902,990 B2 | 3/2011 | Delmonico et al. |
| 8,100,440 B2 | 1/2012 | Yu |
| 8,217,646 B2 | 7/2012 | Karpen |
| 8,276,989 B2 | 10/2012 | Rogers et al. |
| 8,310,604 B2 | 11/2012 | Delmonico et al. |
| 8,343,115 B2 | 1/2013 | Lynch et al. |
| 8,368,749 B2 | 2/2013 | Lambdin et al. |
| 2003/0212308 A1* | 11/2003 | Bendall .......................... 600/131 |
| 2005/0129108 A1 | 6/2005 | Bendall et al. |
| 2008/0152210 A1* | 6/2008 | Bendall .......................... 382/141 |
| 2009/0109045 A1* | 4/2009 | Delmonico et al. ....... 340/636.1 |

OTHER PUBLICATIONS

GE Measurement & Control, XL Go+ Video Probe, Inspection Technologies, 2012, 16 pages.

\* cited by examiner

MODULAR INSPECTION SYSTEM HANDSET

BACKGROUND OF THE INVENTION

The subject matter disclosed herein relates to inspection systems, including modular inspection systems for nondestructive testing.

Nondestructive testing inspection systems can be used to inspect target objects to identify and analyze anomalies in the objects. Nondestructive testing allows an inspection technician to maneuver the probe of an inspection system at or near the surface of the target object in order to perform testing of the object surface and/or the underlying structure. Nondestructive testing can be particularly useful in some industries, e.g., aerospace, power generation, and oil and gas transport or refining, where inspection of target objects preferably takes place without removal of the object from surrounding structures, and where hidden anomalies can be located that would otherwise not be identifiable.

Several different nondestructive testing inspection systems using different modalities are available. For example, visual inspection systems can be used to inspect a target object by placing a video borescope probe with, e.g., an image sensor and imaging optics, proximate to the target object to obtain and display video images of an anomaly. Those video images are then used to analyze the anomaly, including making highly accurate dimensional measurements. Different video borescope probes having different characteristics (e.g., diameters, length, optical characteristics, articulation, etc.) are used depending on the application and the target object.

Eddy current inspection systems can also be used to inspect a target object by placing an eddy current probe with, e.g., an eddy current driver coil generating a changing magnetic field proximate to the surface of the target object. The changing magnetic field induces an eddy current in the target object that can be sensed by a eddy current sensor (e.g., a receiver coil) in the eddy current probe. The presence of anomalies in the target object will cause a change in the eddy current, whose phase and magnitude can be monitored to detect the presence of the anomaly. Different eddy current probes having different characteristics (e.g., diameters, length, frequencies, etc.) are used depending on the application and the target object (e.g., tubing, surface, subsurface, fastener holes, aircraft wheels, welds, etc.).

Ultrasound inspection systems can also be used to inspect a target object by placing an ultrasound probe with, e.g., a transducer transmitting an ultrasonic signal proximate to the surface of a target object. The ultrasonic signal is reflected back from the anomalies of the target object and received by the transducer of the ultrasound probe. The presence of anomalies in the target object will be determined by analyzing the timing and amplitude of the received ultrasonic signals. Different ultrasound probes with transducers having different characteristics (e.g., frequency, pitch, wedge angle, etc.) are used depending on the application and the target object.

Radiographic inspection systems can also be used to inspect a target object using an x-ray or millimeter wave source. In addition, thermographic inspection systems can be used to inspect a target object.

Many of these inspection systems are available as handheld devices (or handsets). In some inspection systems, a particular probe with certain characteristics is permanently attached to the handset. Accordingly, if a different probe is required for a particular inspection, even if that probe is the same modality (e.g., need a videoscope probe of a different diameter or different length or need an eddy current probe having a different frequency), the user will need to obtain an entirely different inspection system rather than being able to substitute just the probe. Similarly, if the probe of an inspection system requires upgrading or replacement, the entire inspection unit, including the handset, must be replaced.

In other inspection systems, the handset is designed to accept different probes from the same modality. For example, a visual inspection system handset can be provided that can operate several different videoscope probes having different characteristics. However, since the visual inspection system handset includes the components to operate the videoscope probes (e.g., articulation, light source, etc.), it cannot be used with other inspection system probes using different modalities and inspection techniques. If a different inspection probe (e.g., an eddy current probe) is required, an entirely different inspection system and handset would be needed rather than being able to substitute just the probe. Similarly, a particular probe can typically only work with a particular handset, which has been designed to operate that particular probe, limiting the flexibility of the probe.

The discussion above is merely provided for general background information and is not intended to be used as an aid in determining the scope of the claimed subject matter.

BRIEF DESCRIPTION OF THE INVENTION

A handset for inspecting a target object with a sensor in an inspection module is disclosed. The handset includes a housing having a grip portion adapted to be held by a person, the housing adapted to selectively mechanically engage with the inspection module, a handset interface on the housing adapted to exchange signals with the inspection module, a handset processor, a user input interface accessible to the person gripping the grip portion and adapted to provide a control signal to the handset processor, and a user output interface responsive to the handset processor to display the data transmitted by the handset processor about the target object.

In one embodiment, a handset for inspecting a target object with a sensor in an inspection module is disclosed. The handset comprises a housing having a grip portion adapted to be held by a person, the housing adapted to selectively mechanically engage with the inspection module, a handset interface on the housing adapted to exchange signals with the inspection module, a handset processor, a user input interface accessible to the person gripping the grip portion and adapted to provide a control signal to the handset processor, and a user output interface responsive to the handset processor to display the data transmitted by the handset processor about the target object.

An advantage that may be realized in the practice of some disclosed embodiments of the handset is that it permits connecting a variety of inspection models to perform inspections in different modalities.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
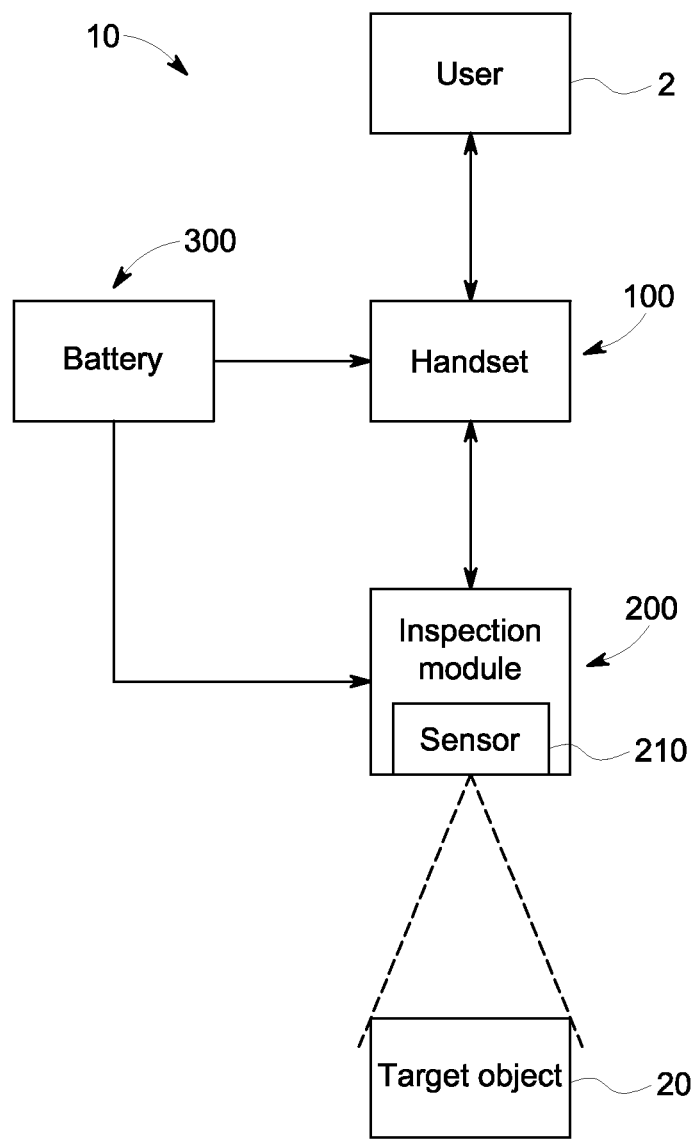
FIG. 1 is a block diagram of an exemplary modular inspection system.

FIG. 1 is a block diagram of an exemplary modular inspection system 10 for inspecting a target object 20. The block diagram is representative of a variety of different modular inspection systems 10 using different modalities and inspection techniques, including, without limitation, visual, eddy current, ultrasound, radiographic, and thermographic inspection systems for nondestructive testing. As will be explained, the inventive modular inspection system 10 allows for inspection of target objects 20 using several of these modalities.

In one embodiment, the user 2 holds handset 100 to conduct an inspection of a target object 20. The handset 100 is adapted to selectively mechanically engage with a housing of an inspection module 200 (or "probe"). A battery 300 is adapted to selectively mechanically engage with the housing of the handset. The handset 100 and inspection module 200 are designed so that they can be selectively attached to or detached from each other to allow one inspection module 200 to be detached from the handset 100 and replaced by a different inspection module 200. For example, a visual inspection module such as a video borescope having a diameter of 3.9 mm, length of 2.0 m, and 80 degree field of view, can be replaced with another visual inspection module having a diameter of 5.0 mm, length of 3.0 m, and 50 degree field of view. Moreover and as will be explained, because the modality-specific hardware and processing for performing an inspection is located in the inspection module 200 (e.g., articulation driver or light source for a video endoscope) rather than in the handset 100, the handset 100 can be used with inspection modules 200 for different modalities (e.g. used with video endoscope probes and eddy current probes).

Referring again to FIG. 1, the inspection module 200 includes at least one sensor 210, which is electrically and mechanically connected to the housing of the inspection module 200. The sensor 210 (e.g., an image sensor in a visual inspection system or a receiver coil in an eddy current inspection system) is adapted to provide sensor data relating to the target object 20 when placed in proximity to the target object 20 in a sensing range of the sensor 210.

Figure 2:
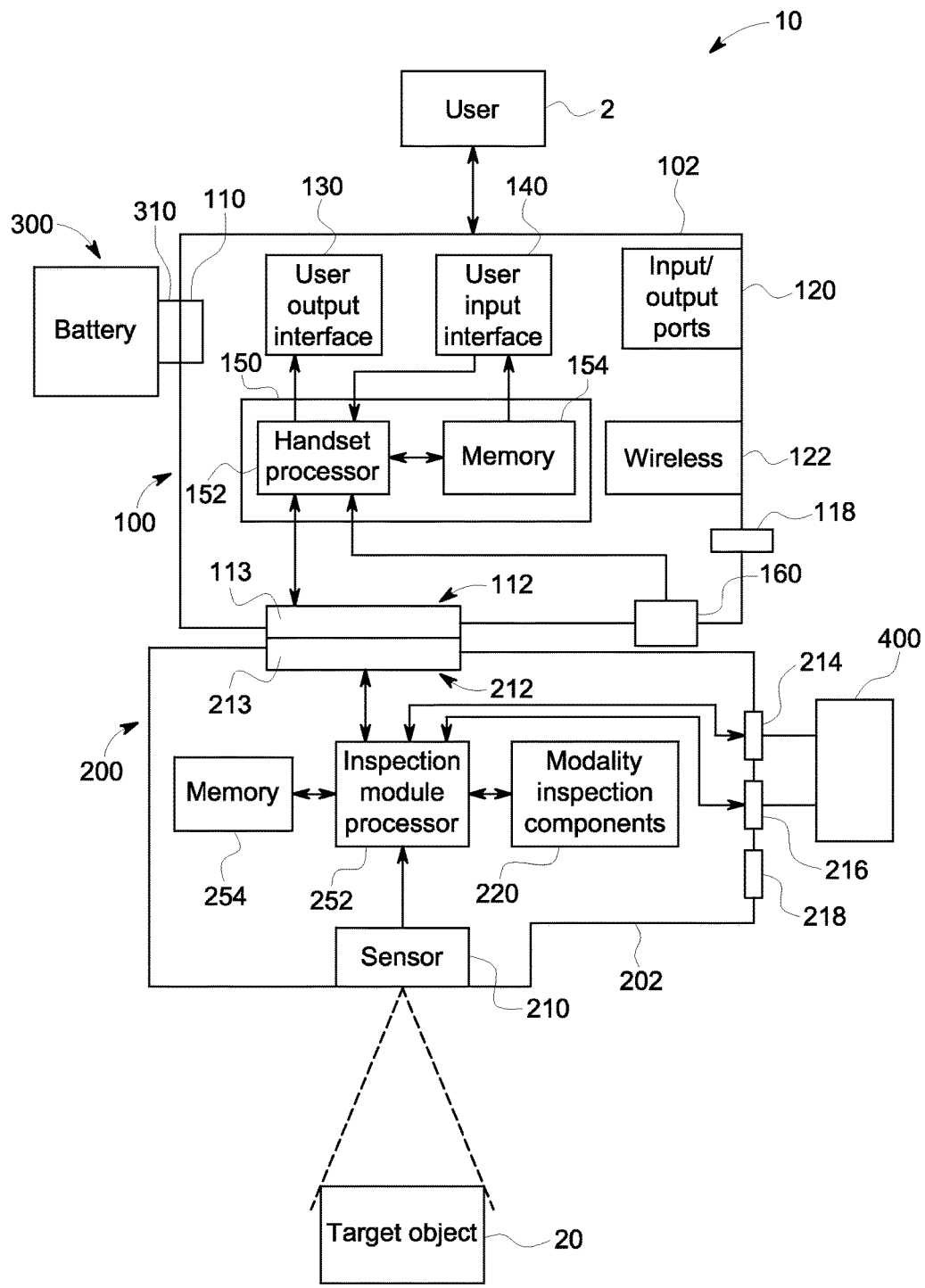
FIG. 2 is a partial schematic of the exemplary modular inspection system of FIG. 1.
Figure 3:
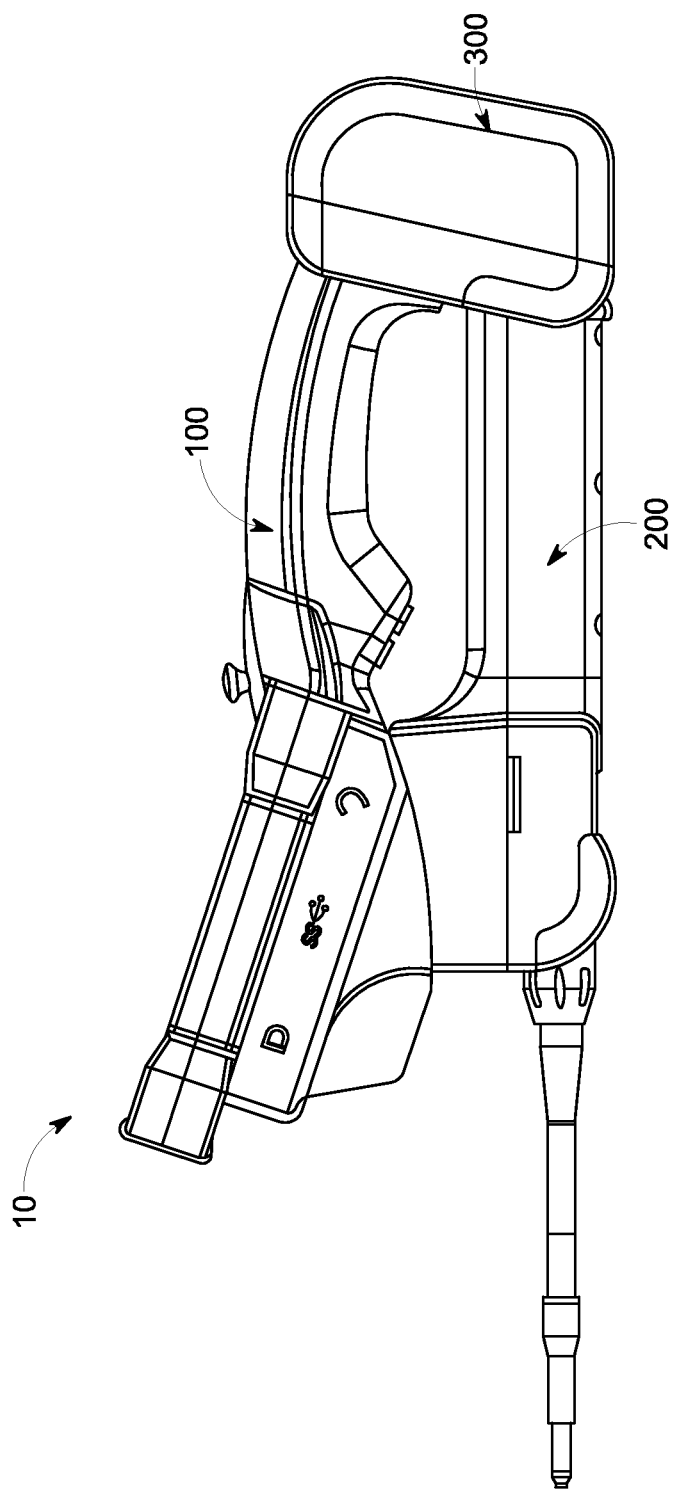
FIG. 3 is a perspective view of the exemplary modular inspection system of FIGS. 1 and 2.

FIG. 2 is a partial schematic of the exemplary modular inspection system 10 of FIG. 1. The exemplary modular inspection system 10 includes a handset 100, an inspection module 200, and a battery 300. FIG. 3 is a perspective view of the exemplary modular inspection system of FIGS. 1 and 2 for an exemplary visual inspection system showing the connections between the handset 100 (FIG. 4), the inspection module 200 (FIG. 5), and the battery 300.

Figure 4:
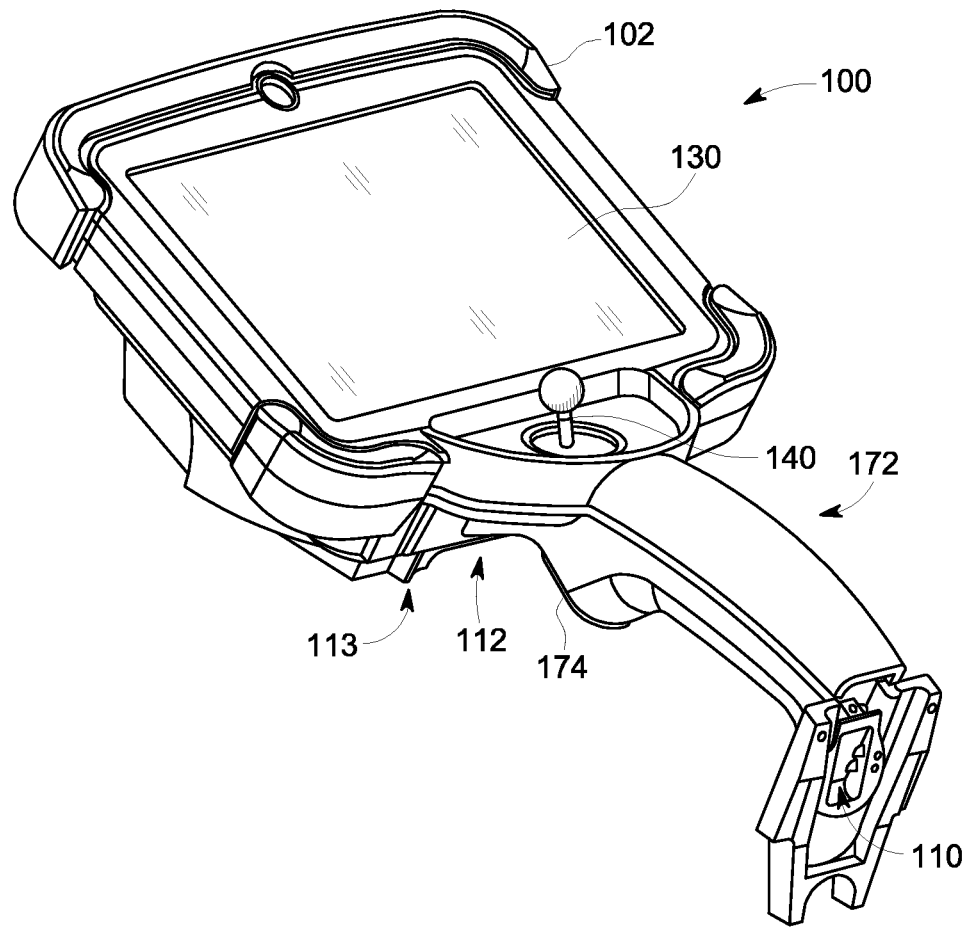
FIG. 4 is a perspective of an exemplary handset for the exemplary modular inspection system of FIG. 3.

Referring to the handset 100 of the modular inspection system 10 shown in FIGS. 2 and 4, it can be seen that the handset 100 does not include any of the modality-specific inspection components 220, which are instead located in the inspection module 200. Since the handset 100 does not include these inspection components 220, the handset 100 can be operated by itself in a way that is similar to a typical computer. For example, the handset 100 is capable of running desktop or embedded versions of commercially available operating systems and can use commercially available software. Accordingly, the handset 100 has the computing power of a modern computer, but in a form factor that can be held and operated in one hand by a user 2. This allows for a handset 100 with a smaller shipping profile, lower cost, and increased productivity in terms of collating data, authoring reports, and transmitting both to other locations.

When receiving sensor data from the inspection module 200, certain parts of the computer hardware of the handset 100 may be programmed to behave differently when an inspection module 200 is attached (e.g., as a dedicated nondestructive testing handset) than when no inspection module 200 is attached (e.g., as a conventional computer). For example, if a visual inspection device is attached to the handset 100, the central processor unit (CPU) and graphics processing unit (GPU) of the handset 100 may be programmed to receive the video data, perform a variety of image processing operations on it such as scaling, deinterlacing, gamma correction, and alpha blending with a graphical overlay, and display this final output continuously via internal or external displays.

In one embodiment and as shown in FIGS. 2 and 3, the modular inspection system 10 includes a selectively-detachable battery 300 having battery power connector 310 for connection to the handset power connector 110 of the handset 100 to convey power when the handset 100 and battery 300 are operatively engaged with each other. In one embodiment, the handset 100 includes an internal battery. In another embodiment, the handset 100 can also include an electrical connector 118 for receiving power from an external power source (AC or DC).

Referring to FIGS. 2 and 4, in one embodiment, the handset 100 includes a computer-on-module (COM) Express single board computer (SBC) 150 containing a handset processor 152 (e.g., an Intel x86 processor), memory 154 (e.g., companion chip DDR3 RAM), and supporting power supplies. The handset 100 can also include a custom carrier board for carrying the SBC, disk, or solid state drives (SSDs). The handset processor 152 can be located in the handset housing 102, e.g., behind a user output interface 130.

In one embodiment, the handset 100 further includes a user input interface 140, which can include one or more of keyboards (full, numeric, or specialty), keypads, joysticks, control buttons, touchpads, touchscreen interface, switches, or other controls. The user input interface 140 can include a sensor associated with a touchscreen interface that presents visual representations of virtual keyboards, joysticks, or other controls such as those described above. Using such a touchscreen, the user 2 can provide inputs as if physical controls were present. The user input interface 140 discussed above is adapted to transmit control signals to the handset processor 152 for controlling the inspection module 200.

As shown in FIG. 4, in one embodiment, the handset housing 102 includes a grip portion 172 adapted to be held by a user 2. The grip portion 172 can be arranged as a hammer grip (as shown) or a pistol grip. The user input interface 140, for example a joystick as shown in FIG. 4, can be positioned so that the user 2 can manipulate the user input interface 140 with the thumb of one hand while grasping grip portion 172 of the handset 100 (FIG. 4) with the fingers of the same hand. The user input interface 140 can also include one or more triggers 174.

In one embodiment, the handset 100 further includes a user output interface 130, which can include, e.g., a visual display (LCD, AMOLED, etc.), speaker, buzzer, or haptic (vibrating) device. The user output interface 130 shown in FIG. 4, a display screen, is arranged in the handset housing 102. In the exemplary embodiment of FIG. 4, the user output interface 130 is responsive to the handset processor 152 to display the output information about the target object 20 to a user 2 based on the packaged data.

The handset 100 can also include input and output ports 120 (Universal Serial Bus (USB), video outputs such as DisplayPort, and audio jacks such as 3.5 mm barrel jacks). In addition, the handset can include wireless network interface 122 (e.g., WiFi Card, Bluetooth Transceiver) for wireless communication. In addition to audio circuitry (CODEC), the handset 100 can also include circuitry to control the power states of the handset 100, the inspection module 200, which can be powered by the handset 100, and other components within the handset 100.

As shown in FIG. 2, in one embodiment, the handset 100 includes a hot-swap detection unit 160 adapted to detect attachment of the inspection module 200 to the handset 100, or detachment of the inspection module 200 from the handset 100. The hot-swap detection unit 160 can be included in the handset processor 152 or can be a separate component. In one embodiment, the hot-swap detection unit 160 is a normally-open momentary switch with a plunger facing the inspection module 200. When the inspection module 200 is operatively engaged with the handset 100, the inspection module 200 presses against the plunger, closing the switch. The handset processor 152 detects the closed switch as an indication that the inspection module 200 is attached. The handset processor 152 can detect the switch state, e.g., by grounding one side of the switch, pulling up the other, and monitoring the voltage of the pulled-up side, which goes low when the inspection module 200 is attached. When the inspection module 200 is detached from the handset 100, the switch opens and the handset processor 152 detects the open switch as an indication that the inspection module 200 is detached.

Figure 5:
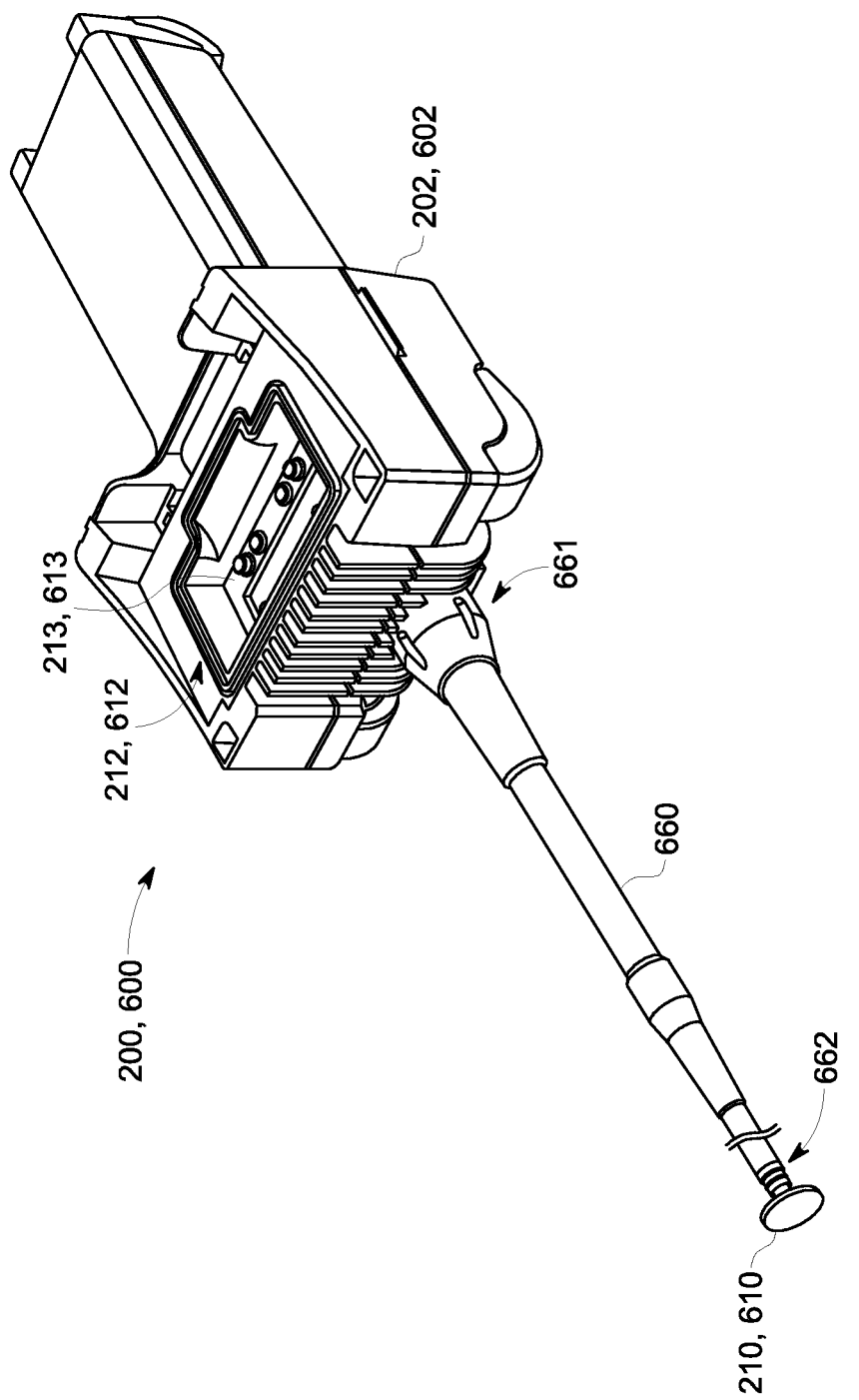
FIG. 5 is a perspective of an exemplary inspection module for the exemplary modular inspection system of FIG. 3.

As shown in FIG. 2, the handset 100 can also include a handset interface 112 for electrically connecting to and exchanging signals (e.g., for data, control, and power) with the inspection module interface 212 of the inspection module 200 (FIG. 5). It will be understood that the handset interface 112 and the inspection module interface 212 (and other devices disclosed herein) can be electrically connected and exchange signals (e.g., electrical, electromagnetic or optical signals) with or without a physical (e.g., metal to metal) connection. For example, an RFID system can provide near field non-contact communications via electrical (e.g., electromagnetic) signals by being having two devices placed in proximity to each other.

The handset interface 112 is adapted to mechanically engage with inspection module interface 212, as the handset connector 113 is operatively arranged with respect to the handset interface 112 to mate or mechanically engage with the inspection module connector 213 in the inspection module interface 212. In one embodiment, the handset connector 113 of the handset interface 112 is disposed at least partly on a surface of the handset housing 102. As shown in FIG. 5, the inspection module connector 213 of the inspection module interface 212 can be mounted in the inspection module housing 202. As will be explained, the handset 100 can transmit power along with proprietary or any of several common standard PC serial interfaces (PCI Express, USB, I2C/SMBUS, UART/COM/RS-232) or parallel interfaces to facilitate the transmission of control commands to the inspection module 200 and to receive data from the inspection module 200.

In one embodiment, the handset interface 112 and the inspection module interface 212 include respective mating connectors 113, 213 for exchanging data signals, control signals, and power. It will be understood that although shown as single connectors in FIG. 2, the handset connector 113 and the inspection module connector 213 can each include multiple connectors (e.g., separate connectors for data, control, and power). For example, the handset connector 113 in the handset interface 112 can include a data connector (e.g., high data rate PCI EXPRESS connector) and a control connector (USB). The handset processor 152 can receive data from the inspection module 200 via the data connector, and transmit a control signal to the inspection module 200 via the control connector. When the inspection module 200 is attached to handset 100 as shown in FIGS. 2 and 3, the data connector and the control connector of the inspection module connector 213 interface with mating connectors in the handset connector 113. For "stand alone" applications where the inspection module 200 is not connected to a handset 100, but instead is attached to a standard computer 400 (e.g., PC, laptop, tablet, etc.), the inspection module may be provided with one or more additional data connectors 214 (e.g., VGA, DVI, HDMI, or DISPLAY-PORT connector) and a control connector 216 (e.g., "B" or "Mini-B" USB connector). In addition, the inspection module 200 can be connected to a standard computer 400 via the inspection module connector 213, which in other applications can be connected to the handset 100 as described previously.

In other embodiments, data signals and control signals are time- or pin-multiplexed in one connector. Data, control, or shared pins, connectors, or data links can be signaled half or full-duplex, and can carry parallel or serialized data. In an example, the control signal connectors are mating USB connectors. As used herein, the term "USB connector" includes connectors that use the signaling protocols of USB over conductors with the same functions (e.g., Vbus, D+, D−, and GND), but have mechanical characteristics that do not conform to the relevant specification.

In one embodiment, the handset connector 113 of the handset interface 112 includes compliant pogo pins that have some degree of travel. The inspection module connector 213 of the inspection module interface 212 includes receiver pads for receiving the pogo pins from the handset connector 113 arranged such that the required characteristic impedance of the specific standard interface is met (e.g., 90 ohms differential impedance is required on USB data pairs).

In one embodiment, the handset interface 112 is only operative when the inspection module 200 is engaged with the handset 100. The hot-swap detection unit 160 of the handset 100 can also be used to detect attachment of the inspection module connector 213 to the handset connector 113, or detachment of the inspection module connector 213 from the handset connector 113.

The connection between the handset connector 113 of the handset interface 112 and the inspection module connector 213 of the inspection module interface 212 creates a purely electrical interface (e.g., no need to transfer motor control or lighting between the handset 100 and the inspection module 200), which minimizes losses and makes sealing easier. In the disclosed embodiment, the handset 100, including the handset interface 112, is rated IP67. In one embodiment, the handset interface 112 is mechanically mated with the inspection module interface 212 using guides, latches, and locks on one or both of the housings 102, 202 of the handset 100 and the inspection module 200.

Referring to the inspection module 200 of the modular inspection system 10 shown in FIGS. 2 and 5, it can be seen that the inspection module 200 includes the modality-specific inspection components 220. Unlike existing solutions where the modality-specific inspection components 220 are located in a handset, inspection modules 200 of different modalities can be used with the same handset 100 in the modular inspection system 10 shown in FIG. 2. The inventive inspection module 200 can more easily be upgraded or replaced without impacting or needing to replace the handset 100.

In one embodiment, the inspection module 200, including the sensor 210, receives power from the handset 100 when the inspection module connector 213 of the inspection module interface 212 is connected to handset connector 113 of the handset interface 112. The inspection module 200 can also include an internal battery. In another embodiment, the handset 100 can include a power connector 118 for receiving power from an external power source (AC or DC).

The inspection module 200 includes inspection module processor 252, which can be located in inspection module housing 202. The inspection module processor 252 is powered by the power received via the module interface 212 or through power connector 218. The inspection module processor 252 can communicate with the handset 100 as described above, providing data and receiving control signals. In one embodiment, the sensor 210 and inspection module processor 252 are separate devices. In other embodiments, the sensor 210 and inspection module processor 252 may be integrated.

In one embodiment, the handset processor 152 (e.g., an INTEL CORE processor) is faster or otherwise more capable than the inspection module processor 252 (e.g., a PICMICRO processor). These embodiments can advantageously offload low-level control from the handset processor 152 to the inspection module processor 252, permitting the handset processor 152 to compute obstacle-avoidance paths or measurements based on captured sensor data or to perform other computationally intensive functions desired by user 2 more rapidly or effectively.

Figure 7:
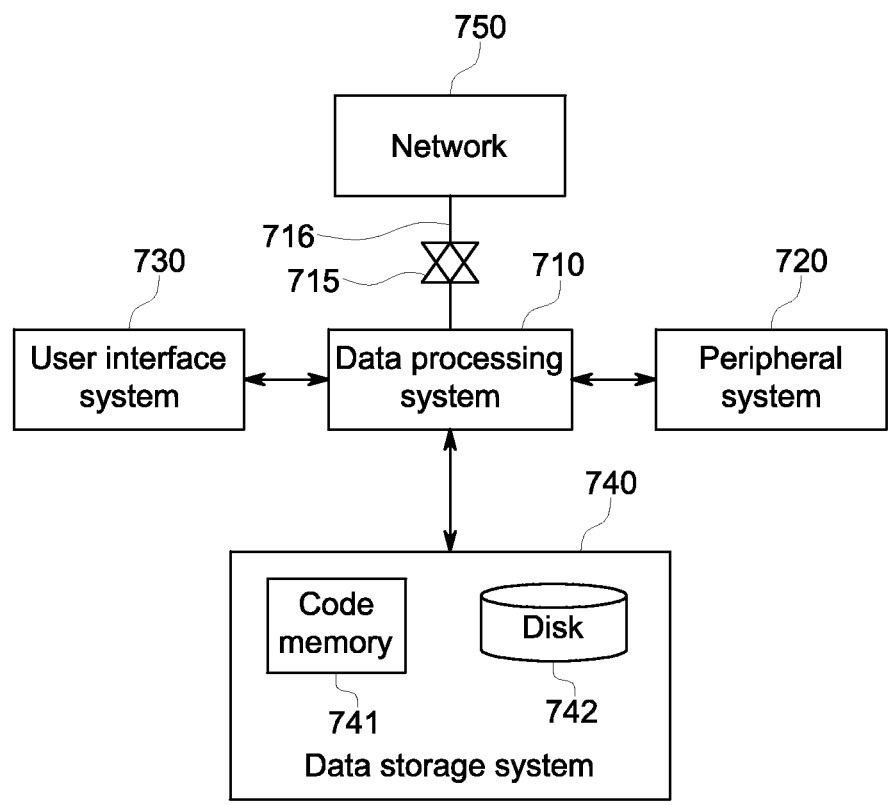
FIG. 7 is a high-level diagram showing a data-processing system and related components.

In one embodiment, the inspection module 200 includes memory 254 for, e.g., storing configuration information. The inspection module processor 252 is adapted to selectively transmit the stored configuration information, e.g., via a connector such as handset connector 213, to the handset 100. The configuration information can describe what sensing modality or modalities the inspection module 200 supports and how the data being transmitted by the inspection module 200 (e.g., packaged data) is formatted. The configuration information can be programmed into memory 254 at the time the inspection module 200 is manufactured, or can be programmed or updated in the field. The memory 254 can be a volatile or nonvolatile memory, e.g., as described herein with reference to data storage system 740 (FIG. 7).

In one embodiment, the sensor data transmitted by the sensor 210 is raw captured data, e.g., video images, eddy current data, ultrasound images, or other data. Since the handset 100 does not include modality inspection components and therefore can be used with inspection modules 200 of different modalities, the sensor data must be formatted (or converted) into packaged data that can be received by the handset processor 152 of the handset 100. The packaged data is sent from the inspection module processor 252 via the inspection module connector 213 of the inspection module interface 212 and the handset connector 113 of the handset interface 112. In one embodiment, the inspection module processor 252 is adapted (e.g., programmed) to receive the sensor data from sensor 210 and transmit corresponding packaged data. The inspection module connector 213 of the inspection module interface 212 is adapted to transmit the packaged data from the inspection module processor 252 to the handset processor 152 via the handset connector 113 of the handset interface 113.

In one embodiment, the inspection module 200 includes an analog front-end (AFE), that can be included in or connected to inspection module processor 252. The AFE can digitize the sensor data, e.g., using an analog to digital (A/D) converter. The AFE can include a sample-and-hold (S/H) unit or a correlated double-sampling (CDS) unit to precondition the inputs to the A/D converter. The AFE can also be included in the sensor 210.

In one embodiment, the dataflow through the modular inspection system 10 starts with the sensor 210 (e.g., an image sensor such as a CCD), which produces sensor data (e.g., analog CCD video or digital video from a packaged CMOS sensor module). The sensor data is received by the inspection module processor 252, which can include, e.g., an A/D converter and/or an AFE. The inspection module processor 252 produces packaged data. The packaged data can be a bit-for-bit or sample-for-sample copy of the sensor data (e.g., produced using a buffer), or a signal boost of the sensor data (e.g., using an amplifier). The packaged data can be produced, e.g., by digitizing the sensor data, sampling the sensor data, sampling data and processing the sampled data with a field-programmable gate array (FPGA) or other programmable device, or any combination.

In one embodiment, the inspection module processor 252 also includes or is connected to a bus transceiver (XCVR) that transmits the packaged data using the digitized sensor data or a transformed version of the digitized sensor data. For example, the inspection module processor 252 or bus transceiver can be programmed or otherwise adapted to transmit a memory-write signal carrying at least some of the packaged data to the handset processor 152 via the module interface 212 and handset interface 112. The packaged data is thus memory-write packets or transactions. In an example, the memory-write signal is a PCI EXPRESS, ISA, EISA, or PCI memory-write signal. In one embodiment, the handset processor 152 is adapted to adjust the received packaged data in response to the control signal to provide information about the target object 20 in a form usable or perceptible by user 2.

When the handset processor 152 in the handset 100 receives the packaged data, it can selectively activate the user output interface 130 to provide the information about the target object 20 in response to the packaged data received via the handset interface 112. The information about the target object 20 can include a direct presentation of the packaged data, or a presentation of a transformation of the packaged data. Therefore, e.g., what the user 2 sees or hears can be a transformed version of the sensor data.

In one embodiment, the handset processor 152 is adapted to automatically receive, and is responsive to, the control signals from the user input interface 140 to provide corresponding control signals to the inspection module processor 252. In response to the received control signal, the handset processor 152 transmits a corresponding control signal to the inspection module 200 via the handset connector 113 of the handset interface 112 and the inspection module connector 213 of the inspection module interface 212. This can be, e.g., a control signal directing an inspection module 200 connected to handset connector 113 to transmit packaged data (e.g., to start image capture). The handset processor 152 is programmed or otherwise adapted to automatically receive packaged data via the handset connector 113 and provide information about the target object 20 corresponding to some or all of the received packaged data. The user output interface 130 then displays the information to the user 2.

This advantageously permits the user 2 to control functions of the inspection module 200 with the handset 100. The handset processor 152 can control the user output interface 130 and independently provide corresponding control signals in response to the user input interface 140, or those functions can be coordinated. For example, the inspection module processor 252 is responsive to the corresponding control signal to adjust the operation of the sensor 210. The inspection module processor 252 can turn the sensor on or off or change its operating parameters. The user input interface 140 can provide control signals corresponding to these functions. The identification of inspection module 200 functions can be stored in the memory 254. In another example, the inspection module processor 252 is responsive to the corresponding control signal to adjust the sensor data to provide the packaged data. For example, the inspection module processor 252 can perform brightness adjustments, e.g., in software or logic.

As mentioned previously and as shown in FIG. 2, for "stand alone" applications where the inspection module 200 is attached or tethered to a standard computer 400, the inspection module is provided with one or more data connectors 214 (e.g., VGA, DVI, HDMI, or DISPLAYPORT connector) and a control connector 216 (e.g., "B" or "Mini-B" USB connector). As also mentioned previously, the inspection module 200 can be connected to a standard computer 400 via the inspection module connector 213. In this "stand alone" configuration, the inspection module 200 can receive control signals from the standard computer 400 and transmit data (e.g., streaming compressed or uncompressed data) to a standard computer 400 for display and storage. A monitor or video-capture device can be connected to the data connector 214. Power can be supplied via the power connector 218. In this way, a user 2 can control the inspection module 200 via a standard computer 400 and receive packaged data in a format for which displays are readily available (e.g., HDMI). This advantageously permits performing inspections using the inspection module 200 both when a handset 100 is available and when a handset 100 is not available.

In one embodiment, the inspection module processor 252 is further adapted to receive an indication of whether the inspection module connector 213 is in use. In one embodiment, inspection module processor 252 receives the indication of whether the inspection module connector 213 is in use by detecting whether or not the handset 100 is electrically connected to the inspection module connector 213. This detection can be done by pin pull-up or pull-down, as discussed above, by measuring waveforms on selected pins, or in other ways.

In various embodiments, if the handset 100 is connected to the inspection module 200, the inspection module processor 252 transmits at least some of first packaged data to the handset processor 152 in the handset 100 (FIG. 2) via the inspection module connector 213. The inspection module processor 252 can transmit the at least some of the first packaged data via a memory write signal, as discussed above. In an example, if the inspection module connector 213 is in use (e.g., the inspection module 200 is connected to the handset 100 (FIG. 2)), packaged data is transmitted via the inspection module connector 213, e.g., using PCI EXPRESS signaling.

If the handset 100 is not connected to the inspection module 200, the inspection module processor 252 transmits at least some of second packaged data to the standard computer 400 (FIG. 2) via the data connector 214. Alternatively, the standard computer 400 may be adapted (not shown) to communicate with the inspection module processor 252 via the inspection module connector 213. The inspection module processor 252 may be adapted to form the second packaged data having a lower data rate than the sensor data (e.g., than the digitized or digital sensor image data). If the inspection module connector 213 is not in use, e.g., because the inspection module 200 is not connected to the handset 100, slower rate packaged data may be transmitted via data connector 214, e.g., a VGA connector or USB connector. In one embodiment, inspection module processor 252 can format the first packaged data and the second packaged data respective data streams, either variable or constant bit rate. The stream of the first packaged data can have a higher peak bit rate than the stream of the second packaged data.

In another example, inspection module processor 252 is adapted to transmit data at less than full bit rate via control connector 216, e.g., as an isochronous USB data stream. In this way, a standard computer 400 with appropriate software can control inspection module 200 and receive packaged data using a single connection. The inspection module processor 252 can be configured to operate as a standard USB device, e.g., a device implementing a vendor-specific USB device class for receiving control signals, and the standard Video USB device class for providing information about the target object 20 via video. This permits performing inspections with only standard computer hardware and no handset 100.

Figure 6:
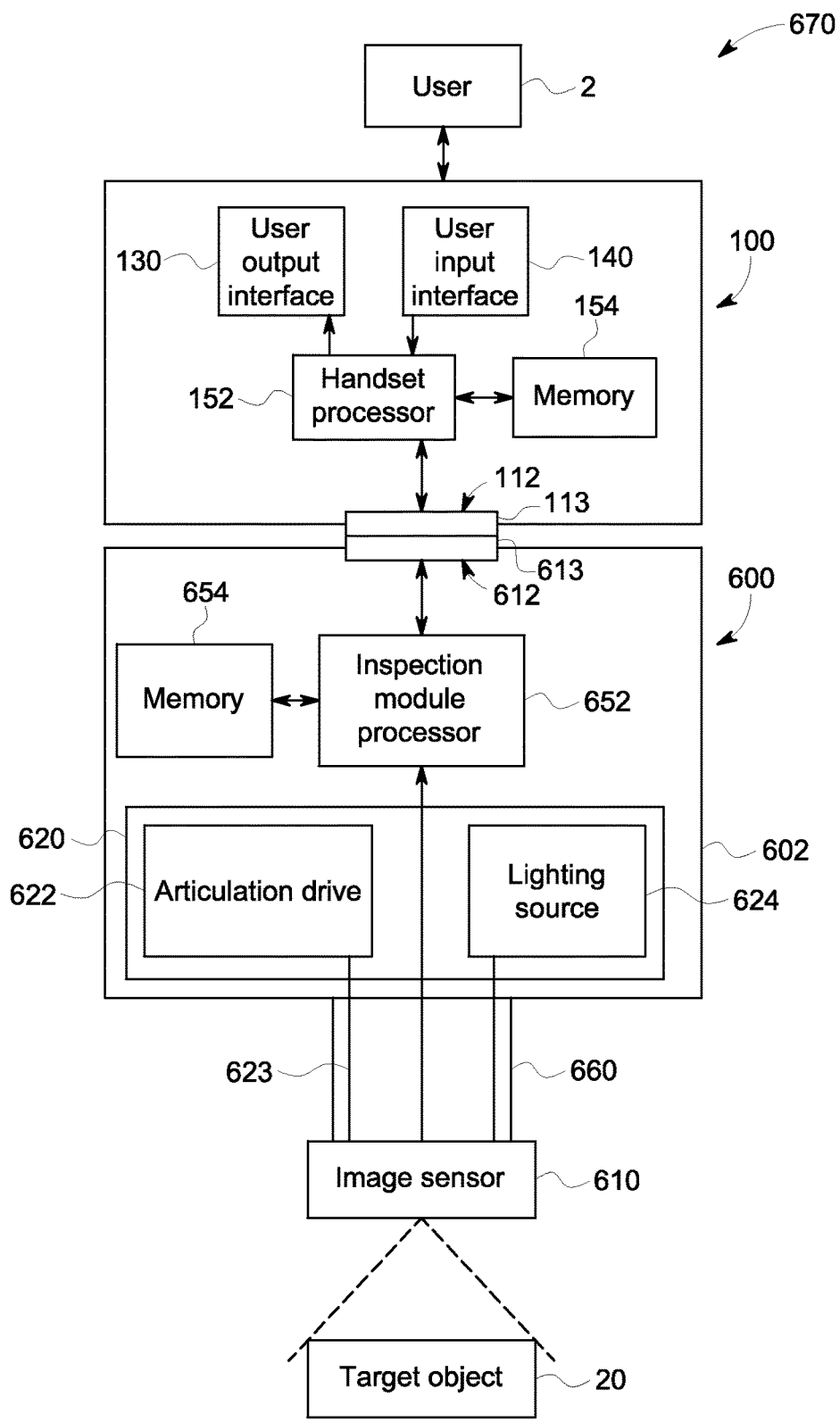
FIG. 6 is a partial schematic of an exemplary modular inspection system for a visual inspection system.

As explained and as shown in FIG. 2, the inventive modular inspection system 10 allows the same handset 100 to be used with inspection modules 200 of different modalities. FIG. 6 is a partial schematic of an exemplary modular inspection system 670 for a visual inspection system. As can be seen in a comparison with FIGS. 2 and 4, the same handset 100 is used with the common exemplary components (e.g., the handset interface 112, the handset connector 113, user output interface 130, user input interface 140, handset processor 152, and memory 154).

Turning to the visual inspection module 600 of FIG. 6, the visual inspection module 600 (also shown in FIG. 5) includes an inspection module housing 602, inspection module interface 612, and inspection module connector 613, which operate similarly to those generic components in FIG. 2 described previously. However, to provide the visual inspection capabilities in the inspection module 600, the inspection module processor 652 and memory 654 must be tailored to provide visual inspection (modality specific) capabilities in the visual inspection module 600 along with the visual inspection components 620. For example, the visual inspection components 620 can include, without limitation, the articulation drive 622 and related components (motors, servomotors, pneumatic controls), and the light source 624 (LEDs, Lasers, lamps) and related components (light engine controls). In addition, the visual inspection components 620 include without limitation light source control (e.g., power supplies for proximal or distal illumination sources), measurement engine power supplies and controls, CCD and CMOS imager video reconstruction and processing circuits, digital image chain components such as FPGAs and DSPs, and a plurality of embedded controllers to manage the modality-specific functions of the probe. As explained, these visual inspection components 620 would typically be found in the handset of existing systems, which cannot be used with inspection modules of different modalities.

Referring again to FIG. 6, the sensor 610 for the visual inspection module is an image sensor (e.g., CCD), which can provide sensor data in the form of analog video. The inspection module processor 652 receives the sensor data and is adapted to provide a visual representation of the sensor data as the packaged data to be transmitted to the handset processor 152 via the inspection module connector 213 of the inspection module interface 212 and the handset connector 113 of the handset interface 112. The handset processor 152 is adapted to provide image data corresponding to the packaged data as the information about the target object 20 to be displayed on the visual display in the user output interface 130 of the handset 100.

The inspection module processor 652 receives the sensor (image) data from the image sensor 610, produces packaged data corresponding to the received sensor data, and selectively transmits the packaged data to the handset 100. For example, the packaged data can be digital image data corresponding to the analog or digital video data. The digital image data can be packed in a video compression format, e.g., ITU-T H.262 or ISO/IEC 14496 formats. The inspection module processor 652 can compensate for nonuniformity (FPN, fixed-pattern noise) and provide digital data of the imaged pixels. The inspection module processor 652 can also receive commands to select only a portion of the sensor data to be read out, to enable or disable the nonuniformity compensation, or produce a test image. In one embodiment, the inspection module processor 652 is adapted to perform color-correction or gamma adjustment on the video data from the image sensor 610 and provide results or transformed results thereof as the packaged data. The inspection module processor 652 can do so in response to the corresponding control signal, when triggered by a timer, in response to a user control, or continuously.

In one embodiment, the handset processor 152 is adapted to receive control signals from the user input interface 140 and provide a control signal to the inspection module processor 652 of the visual inspection module 600. For example, a control signal from user input interface 140 can be a brightness control signal, wherein the inspection module processor 652 adds to or subtracts from each pixel's data a value corresponding to the brightness control signal. Similarly, in order to control the light source 624 in the visual inspection module 600, the handset processor 152 is adapted to transmit a control signal from the user input interface 140 of the handset 100. In another embodiment, the user input interface 140 (e.g., joystick) can provide a control signal to the handset processor 152 for controlling the articulation drive 622 in the inspection module 600. The handset processor 152 can then provide an articulation control signal communicating the steering mode and joystick position to the inspection module processor 652, which then generates a corresponding motor command to control the articulation drive 622 in the inspection module. In another embodiment, the control signal from the user input interface 140 could be an acquire data from the sensor command or stop acquiring data from the sensor command. If the handset processor 152 receives a stop acquiring data from the sensor command, the handset processor 152 could provide a corresponding control signal to the inspection module processor 652 to reduce power in the inspection module 600 (e.g., instruct the inspection module processor 652 to turn off the lighting source 624).

As shown in FIGS. 5 and 6, the sensor 610 is attached to inspection module housing 602, e.g., via support member 660. In one embodiment, the sensor 610 is connected to the distal end 662 of elongated support member 660. The proximal end 661 of the support member 660 is connected to the inspection module housing 602. The support member 660 can include an insertion tube and can have an orientation-controllable distal end 662. Alternatively, the support member 660 can be designed so most or substantially all of the support member 660 moves or orients to control the orientation of the distal end 662. In this example, as shown, the inspection module 600 does not include a user input interface or a user output display. The inspection module 600 can advantageously be used with a handset 100 should a visual display be desired.

Referring to FIG. 6, the inspection module 600 includes an articulation drive 622. In some embodiments, the articulation drive 622 is located in the inspection module housing 602 and receives power from a power-providing device. Forcing member 623 is connected to articulation drive 622 and adapted to transmit force from articulation drive 622 along support member 660 to control the orientation of the distal end of support member 660, and thus to control the orientation of image sensor 610. The forcing member 623 is represented graphically on FIG. 6 and can include one or more pushrods, belts, chains, bladders, hydraulic or pneumatic lines, or other force-transmitting components. In an example, the articulation drive 622 includes motors and forcing member 623 includes cables adapted to control the orientation of the distal end of the support member 660. In one embodiment, a detachable tip is attached to the distal end of support member 660, and image sensor 610 is located in the detachable tip.

The articulation drive 622 and forcing member 623 (or more than one articulation drives 622 or forcing members 623) can be used to perform adjustments in any or all of the three degrees of position freedom and the three degrees of orientation freedom, and any or all other mechanical degrees of freedom of support member 660 or image sensor 610 (e.g., optical zoom of image sensor 610, or multiple joints of a jointed support member 660). The inspection module processor 652 is adapted to receive a control signal and to automatically control articulation drive 622 in response to the received control signal.

Referring to FIG. 6, the inspection module 600 includes a light source 624 located in the inspection module housing 602. The light source 624 receives power from a power-providing device and illuminates the target object 20. An optical fiber can extend along the support member 660 and be coupled to the light source 624 to convey light from the light source 624 to the distal end 662 (FIG. 5) of the support member 660 to illuminate the target object 20. In some embodiments, the inspection module processor 152 of the handset 100 receives a control signal from the user input interface 140 and automatically controls the light source 624 in response to the received control signal. In one embodiment, the received control signal is an illumination control signal indicating a change in illumination desired by user 2 (e.g., brighter, darker, change wavelength, change pattern). The handset processor 152 is adapted to provide a light source command as the corresponding control signal in response to the received illumination control signal.

While the exemplary modular inspection system 670 of FIG. 6 is for visual inspection, it will be understood that the inventive modular inspection system can be used for other modalities, including eddy current, ultrasound, radiographic, and thermographic inspection systems. For example, in an eddy current inspection system, the sensor 210 (FIG. 2) can be an eddy current probe having an eddy current driver coil and an eddy current sensor (e.g., receiver coil). In an ultrasound inspection system, the sensor 210 can be an ultrasonic transducer. In a radiographic inspection system, the sensor 210 can include an x-ray or millimeter wave source or detector.

In another example based on FIG. 2, the sensor 210 can be a temperature sensor. In this example, the handset processor 152 commands the user output interface 130 to provide an audible or tactile alert if the temperature measured by the sensor 210 exceeds a selected threshold. This has various advantages. For example, it is sometimes desirable to inspect jet engines directly after engine shutdown while an aircraft is parked at an airport-terminal gate. Using the temperature sensor permits readily determining whether the engine temperature is still higher than the temperature the inspection module 200 can tolerate. This advantageously reduces the time spent waiting for the engine to cool. Instead of waiting a known time that includes a safety margin, the engine temperature can be tested periodically, and inspection (e.g., visual inspection) can proceed as soon as the temperature is within the operating range of inspection module 200 (or the components thereof that are exposed to the residual heat in the engine).

FIG. 7 is a high-level diagram showing the components of a data-processing system for analyzing data and performing other analyses described herein. The system includes a data processing system 710, a peripheral system 720, a user interface system 730, and a data storage system 740. The peripheral system 720, the user interface system 730 and the data storage system 740 are communicatively connected to the data processing system 710. Data processing system 710 can be communicatively connected to network 750, e.g., the Internet or an X.25 network, as discussed below. A controller carrying out operations described above can include one or more of systems 710, 720, 730, or 740, and can connect to one or more network(s) 750. For example, the handset processor 152 or inspection module processor 252 (FIG. 3), can each include system 710 and one or more of systems 720, 730, or 740.

The data processing system 710 includes one or more data processors that implement processes of one embodiment described herein. A "data processor" is a device for automatically operating on data and can include a central processing unit (CPU), a desktop computer, a laptop computer, a mainframe computer, a personal digital assistant, a digital camera, a cellular phone, a smartphone, or any other device for processing data, managing data, or handling data, whether implemented with electrical, magnetic, optical, biological components, or otherwise.

The phrase "communicatively connected" includes any type of connection, wired or wireless, between devices, data processors, or programs in which data can be communicated. Subsystems such as peripheral system 720, user interface system 730, and data storage system 740 are shown separately from the data processing system 710 but can be stored completely or partially within the data processing system 710.

The data storage system 740 includes or is communicatively connected with one or more tangible non-transitory computer-readable storage medium(s) configured to store information, including the information needed to execute processes according to one embodiment. A "tangible non-transitory computer-readable storage medium" as used herein refers to any non-transitory device or article of manufacture that participates in storing instructions which may be transmitted to data processing system 710 for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM). Storage media can store data electronically, magnetically, optically, chemically, mechanically, or otherwise, and can include electronic, magnetic, optical, electromagnetic, infrared, or semiconductor components.

Embodiments of the present invention can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct data processing system 710 to perform a particular series of operational steps when loaded, thereby implementing functions or acts specified herein.

In an example, data storage system 740 includes code memory 741, e.g., a random-access memory, and disk 742, e.g., a tangible computer-readable storage device such as a hard drive or solid-state flash drive. Computer program instructions are read into code memory 741 from disk 742, or a wireless, wired, optical fiber, or other connection. Data processing system 710 then executes one or more sequences of the computer program instructions loaded into code memory 741, as a result performing process steps described herein. In this way, data processing system 710 carries out a computer implemented process that provides for a technical effect of measuring geometric characteristics of the target object 20 and determining the physical condition of a remote visual inspection system. This condition (accurate or not) can then be reported to a user. In one embodiment, blocks of the flowchart illustrations or block diagrams herein, and combinations of those, can be implemented by computer program instructions.

Computer program code can be written in any combination of one or more programming languages, e.g., Java, Smalltalk, C++, C, or an appropriate assembly language. Program code to carry out methods described herein can execute entirely on a single data processing system 710 or on multiple communicatively-connected data processing systems 710. For example, code can execute wholly or partly on a user's computer and wholly or partly on a remote computer, e.g., a server. The remote computer can be connected to the user's computer through network 750. The user's computer or the remote computer can be non-portable computers, such as conventional desktop personal computers (PCs), or can be portable computers such as tablets, cellular telephones, smartphones, or laptops.

The peripheral system 720 can include one or more devices configured to provide digital content records or other data to the data processing system 710. For example, the peripheral system 720 can include digital still cameras, digital video cameras, cellular phones, or other data processors. The data processing system 710, upon receipt of data from a device in the peripheral system 720, can store such data in the data storage system 740.

The user interface system 730 can include a mouse, a keyboard, another computer (connected, e.g., via a network or a null-modem cable), a microphone and speech processor or other device(s) for receiving voice commands, a camera and image processor or other device(s) for receiving visual commands, e.g., gestures, or any device or combination of devices from which data is input to the data processing system 710. In this regard, although the peripheral system 720 is shown separately from the user interface system 730, the peripheral system 720 can be included as part of the user interface system 730.

The user interface system 730 also can include a display device, a processor-accessible memory, or any device or combination of devices to which data is output by the data processing system 710. In this regard, if the user interface system 730 includes a processor-accessible memory, such memory can be part of the data storage system 740 even though the user interface system 730 and the data storage system 740 are shown separately in FIG. 7.

In one embodiment, data processing system 710 includes communication interface 715 that is coupled via network link 716 to network 750. For example, communication interface 715 can be an integrated services digital network (ISDN) card or a modem to provide a data communication connection to a corresponding type of telephone line. As another example, communication interface 715 can be a network card to provide a data communication connection to a compatible local-area network (LAN), e.g., an Ethernet LAN, or wide-area network (WAN). Wireless links, e.g., WIFI or GSM, can also be used. Communication interface 715 sends and receives electrical, electromagnetic or optical signals that carry digital data streams representing various types of information across network link 716 to network 750. Network link 716 can be connected to network 750 via a switch, gateway, hub, router, or other networking device.

Network link 716 can provide data communication through one or more networks to other data devices. For example, network link 716 can provide a connection through a local network to a host computer or to data equipment operated by an Internet Service Provider (ISP).

Data processing system 710 can send messages and receive data, including program code, through network 750, network link 716 and communication interface 715. For example, a server can store requested code for an application program (e.g., a JAVA applet) on a tangible non-volatile computer-readable storage medium to which it is connected. The server can retrieve the code from the medium and transmit it through the Internet, thence a local ISP, thence a local network, thence communication interface 715. The received code can be executed by data processing system 710 as it is received, or stored in data storage system 740 for later execution.

Figure 8:
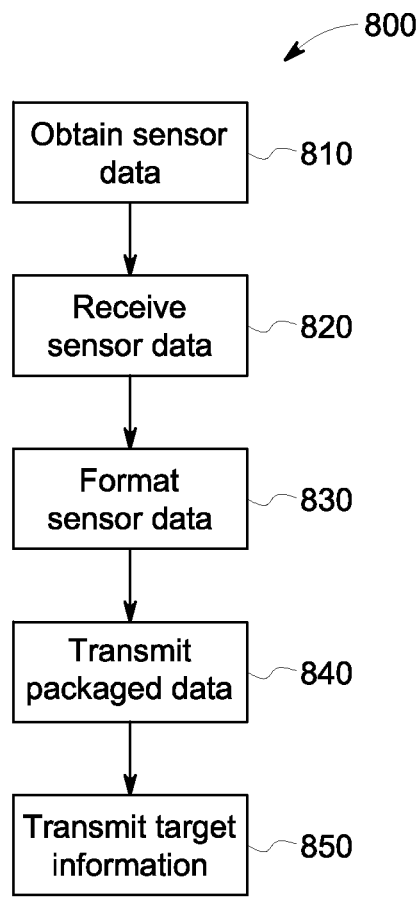
FIG. 8 is a flow diagram of an exemplary method of inspecting a target object using an inspection module and a handset.

FIG. 8 is a flow diagram of an exemplary method 800 of inspecting a target object 20 using an inspection module 200 and a handset 100. At step 810, the sensor 210 (e.g., an image sensor) in the inspection module 200 located proximate to the target object 20 obtains sensor data (e.g., image data). At step 820, the inspection module processor 252 in the inspection module 200 receives the sensor data. At step 830, the inspection module processor 252 formats the sensor data to provide packaged data. At step 840, the inspection module processor 252 transmits the packaged data to the handset processor 152 in the handset 100. At step 850, the handset processor 152 transmits information about the target object 20 based on the packaged data to the user output interface 130.

In view of the foregoing, various embodiments of the invention capture sensor data of a physical target object. A technical effect is to permit determining or measuring properties of target objects. Doing so advantageously permits, e.g., determining the condition of an object that is difficult or hazardous to access or otherwise cannot be determined.

In the description herein, some embodiments will be described in terms that would ordinarily be implemented as software programs. Those skilled in the art will readily recognize that the equivalent of such software can also be constructed in hardware (hard-wired or programmable), firmware, or micro-code. Accordingly, embodiments of the present invention may take the form of an entirely hardware embodiment, an entirely software embodiment (including firmware, resident software, or micro-code), or an embodiment combining software and hardware embodiments. Software, hardware, and combinations can all generally be referred to herein as a "service," "circuit," "circuitry," "module," or "system." One embodiment can be embodied as systems, methods, or computer program products. Because data manipulation algorithms and systems are well known, the present description will be directed in particular to algorithms and systems forming part of, or cooperating more directly with, systems and methods described herein. Other embodiments of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any embodiment is conventional and within the ordinary skill in such arts.

The invention is inclusive of combinations of the embodiments or embodiments described herein. References to "a particular embodiment" or "embodiment" and the like refer to features that are present in at least one embodiment of the invention. Separate references to "an embodiment" or "particular embodiments" or "embodiments" or the like do not necessarily refer to the same embodiment or embodiments; however, such embodiments are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

This written description uses examples to disclose the invention, including the best mode, and also to enable any person skilled in the art to practice embodiments of the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A handset for inspecting a target object with an inspection modality not found in the handset using an inspection module having a sensor, the inspection module comprising a modality-specific inspection component having a modality-specific hardware, modality-specific processing functions, modality-specific configuration information, and modality-specific sensor information, and the handset comprising:
    a handset interface configured to exchange signals with the inspection module;
    a handset processor, the handset processor configured to receive information for supporting the inspection modality not found in the handset from the inspection module, including the handset processor being configured to:
        receive the modality-specific configuration information and the modality-specific sensor information from the modality-specific hardware of the inspection module; and
        control the modality-specific processing functions of the inspection module, wherein the modality-specific configuration information of the inspection module includes data formatting information for the inspection modality not found in the handset;
    a user input interface configured to provide a control signal to the handset processor to control the modality-specific hardware of the inspection module; and
    a user output interface responsive to the handset processor to display the modality-specific sensor information about the target object using the modality-specific processing functions and the modality-specific configuration information including the data formatting information for the inspection modality not found in the handset.

2. The handset of claim 1, further comprising a housing having a grip portion configured to be held by a person, the housing configured to selectively mechanically engage with the inspection module, wherein the grip portion is arranged as one of a hammer grip or a pistol grip.

3. The handset of claim 1, wherein the handset interface comprises a handset connector.

4. The handset of claim 3, wherein the handset connector comprises one of a pogo pin or a conductive pad for receiving a pogo pin.

5. The handset of claim 1, wherein the control signal is at least one of a steering mode or a joystick position, and the handset processor is configured to provide an articulation control signal to the inspection module.

6. The handset of claim 1, wherein the control signal is a light control signal, and the handset processor is configured to provide a light source command to the inspection module.

7. The handset of claim 1, wherein the control signal is a stop acquiring data from the sensor control signal, and the handset processor is configured to provide a command to the inspection module to reduce power in the inspection module.

8. The handset of claim 1, wherein the handset processor is configured to automatically receive the control signal from the user input interface, in response to the received control signal, provide a modality specific control signal via the handset interface to the inspection module, receive the modality-specific sensor data via the handset interface from the inspection module; and automatically provides the received modality-specific sensor information to the user output interface.

9. The handset of claim 1, wherein the handset is configured to provide electrical power to the sensor.

10. The handset of claim 1, wherein the sensor is an image sensor and the handset does not include an articulation driver configured to move the sensor.

11. The handset of claim 1, wherein the sensor is an image sensor and the handset does not include a light source configured to illuminate the target object.

12. The handset of claim 1, wherein the handset is configured to selectively mechanically engage with a battery.

13. The handset of claim 1, wherein the user input interface comprises a touchscreen interface.

14. The handset of claim 1, wherein the user input interface comprises one or more of a joystick and a button.

15. The handset of claim 1, further comprising a wireless network interface.

16. The handset of claim 1, further comprising one or more of input ports and output ports.

* * * * *